United States Patent [19]

Lognion

[11] Patent Number: 4,496,356
[45] Date of Patent: Jan. 29, 1985

[54] ANAL EXCRETION COLLECTING RECTAL CATHETER

[76] Inventor: Leon Lognion, 2730 E. Lucas Dr., Beaumont, Tex. 77703

[21] Appl. No.: 426,999

[22] Filed: Sep. 29, 1982

[51] Int. Cl.$^3$ ............................................. A61F 5/44
[52] U.S. Cl. .................................................. 604/328
[58] Field of Search ......................... 128/760, 767–769, 128/DIG. 24, DIG. 25; 604/327, 328, 355, 346–349, 332, 317–320

[56] References Cited

U.S. PATENT DOCUMENTS

| | | | |
|---|---|---|---|
| 3,570,490 | 3/1971 | Berger | 604/332 |
| 3,934,575 | 1/1976 | Bucalo | 128/769 |
| 3,938,521 | 2/1976 | Ritota et al. | 604/328 |
| 4,030,500 | 6/1977 | Ronnquist | 604/328 |
| 4,354,494 | 10/1982 | Hogin | 604/349 |

FOREIGN PATENT DOCUMENTS

| | | |
|---|---|---|
| 111720 | 12/1928 | Austria . |
| 36015 | 1/1909 | Fed. Rep. of Germany ...... 604/349 |
| 867582 | 2/1953 | German Democratic Rep. .................................... 604/349 |

Primary Examiner—C. Fred Rosenbaum
Assistant Examiner—J. L. Kruter
Attorney, Agent, or Firm—Roylance, Abrams, Berdo & Goodman

[57] ABSTRACT

A device insertable in the anal orifice of a patient for collecting excretions from the orifice comprises an excretion receiving tube with open and closed ends, a ring of resilient material fixed to the tube open end, and a thin, elongated flexible member. The flexible member has one end secured to the ring and extends exteriorly of the tube such that the device can be easily removed from the orifice in the patient by pulling the flexible member.

8 Claims, 3 Drawing Figures

U.S. Patent  Jan. 29, 1985  4,496,356
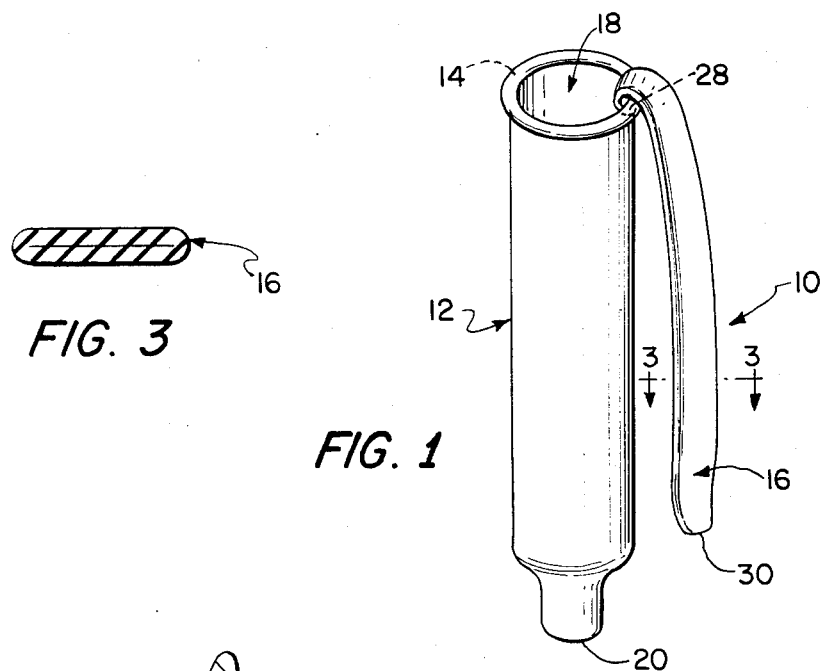
FIG. 3
FIG. 1
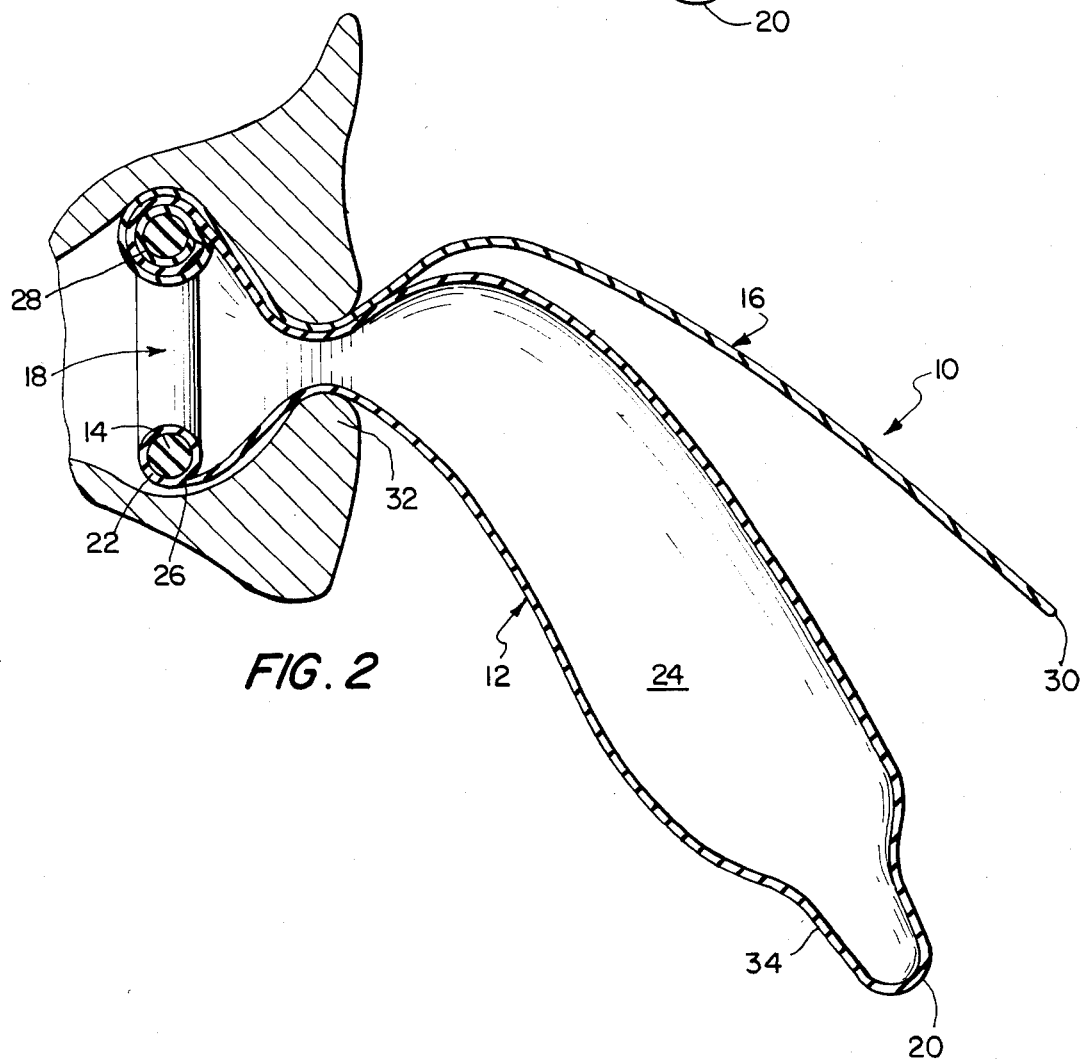
FIG. 2

ANAL EXCRETION COLLECTING RECTAL CATHETER

The present invention relates a device insertable in an orifice in a patient for collecting excretions from the orifice.

BACKGROUND OF THE INVENTION

For persons confined to a bed or otherwise unable to use normal toilet facilities in a conventional bathroom, a bowel movement is often painful, embarrassing, frustrating and complicated. Conventional bedpans require the patient to be placed in an uncomfortable position and are difficult to use causing the patient considerable embarrassment and pain.

Several devices have been development attempting to overcome the disadvantages associated with bedpans. These devices are insertable into the patient's rectum and comprise a bag or closed end tube which receives the fecal matter. Typical examples of such devices are disclosed in U.S. Pat. No. 4,182,332 to Delaney, U.S. Pat. No. 4,030,500 to Ronnquist and U.S. Pat. No. 3,548,828 to Vasile and U.S. Pat. No. 3,938,521 to Ritota et al.

However, conventional excretion collecting devices or rectal catheters are difficult and painful to place into and remove from the patient, are uncomfortable to the patient while in place, and are unduly complex causing them to be difficult and expensive to manufacture. The complex arrangement of the conventional devices also make them difficult to operate. Their relatively high cost prevents the conventional devices from being readily used in a disposable manner.

BRIEF DESCRIPTION OF THE INVENTION

An object of the present invention is to provide a device for collecting excretions from an orifice in a patient which can be easily, safely, gently and securely located and removed from the orifice of the patient.

Another object of the present invention is to provide a device for collecting excretions which is inexpensive permitting it to be economically used in a disposable fashion.

A further object of the present invention is to provide a device for collecting excretions which is simple and inexpensive to manufacture.

An additional object of the present invention is to provide a device for collecting excretions which can be used in a sanitary manner.

Other objects, advantages and salient features of the present invention will become apparent from the following detailed description of a preferred embodiment of the invention.

Briefly described the invention includes a device insertable in an orifice in a patient for collecting excretions from the orifice comprising an excretion receiving tube, a ring of resilient material, and a thin, elongated flexible member. The receiving tube has opened and closed ends with the ring fixed to the tube open end. The flexible member has one end secured to the ring and extends exteriorly of the tube.

The device can be inserted within the patient's orifice by lubricating and collapsing the resilient ring, and then inserting it into the body orifice, e.g., the anus, in the same manner as a suppository. The ring is pushed in with one finger until it is completely inserted into the rectum where the ring will return to its relaxed, round shape securing the device within the anal opening. The receiving tube can be formed of thin, very flexible material which will conform to the anal walls, but which cannot be pulled out because of the ring.

In this manner, the device is undetectable to the patient and does not irritate or otherwise bother the patient while collecting waste from the rectum. The bag may be emptied by opening the closed end of the bag such that it can be resealed by clamping for reuse. When the device is to be removed from the patient, the flexible member, which extends out of the anus exteriority of the tube and conforms to the anal walls, is pulled causing the ring to deform and move in a manner which facilitates removal from the body.

Moreover, a simple construction of the device permits it to be easily and inexpensively manufactured such that it can be used in a disposable manner.

BRIEF DESCRIPTION OF THE DRAWINGS

In order that the manner in which the foregoing and other objects are attained in accordance with the invention can be understood in detail, a particular advantageous embodiment thereof will be described with reference to the accompanying drawings, which form a part of this application, and wherein:

FIG. 1 is a perspective view of a device for collecting excretions in accordance with the present invention;

FIG. 2 is a side elevational view in section of the device of FIG. 1 located in a body orifice; and FIG. 3 is an enlarged cross-sectional view of the flexible member taken along lines 3—3 of FIG. 1.

DETAILED DESCRIPTION OF THE PREFERRED EMBODIMENT OF THE INVENTION

Referring to FIGS. 1 and 2, a device, insertable in an orifice in a patient, for collecting excretions from the orifice comprises three basic parts, an excretion receiving tube 12, a ring of resilient material 14 and a thin, elongated flexible member 16. Receiving tube 12 has an open end 18 fixed to resilient ring 14 and an opposite closed end 20. Ring 14 is formed of pliable rubber in the shape of a solid, circular O-ring. The thickness of the ring (i.e., the transverse cross-sectional diameter of the O-ring) is approximately one-quarter inch, while the O-ring is approximately one and one-half inches in diameter.

Receiving tube 12 is formed of a rubberized, elongated and thin walled tube which is adhered to ring 14 with a suitable adhesive. The tube is approximately ten inches long. The portion 22 of tube 12 adjacent its open end 18 extends about the exterior of the ring and into the tube interior 24. In this manner, tube portion 22 covers substantially the entire surface of the ring with its end 26 located within the tube. This connection of the tube to the ring provides a smooth exterior surface on the device which will not irritate or otherwise bother the patient.

Flexible member 16 is formed of a pliable, rubberized elongated thin walled tube similar to, but smaller than, receiving tube 12. One end 28 is attached to ring 14 and extends exteriorly of tube 12 terminating in a closed member end 30 detached from tube 12. The use of a collapsed tube to form flexible member 16 eliminates sharp edges which would irritate the patient.

Flexible member end portion 28 is bonded by a suitable adhesive directly to ring 14, as illustrated in FIG. 2. The attachment of end portion 28 extends along only a minor arcuate portion of ring 14, as illustrated in FIG. 1. Preferably, the attachment of flexible member 16 to ring 14 extends for less than about 90 degrees, but more than about 45 degrees, of the circumference of the ring.

Flexible end member 28 extends about and is bonded to the entire thickness of the arcuate portion of the ring as illustrated in FIG. 2, and is arranged such that member end portion 28 terminates within tube interior 24. From member end 28, the flexible member extends out and over tube open end 18. No adhesive is provided between tube 12 and flexible member 16 such that the flexible member merely overlies the tube adjacent open end 18 and is freely movable relative to the exterior of tube 12. This attachment of flexible member 16 to ring 14 simplifies the manufacture of the device and improves the operation of member 16 during removal of the device 10 from a body orifice 32.

Device 10 is inserted into body orifice 32 by lubricating and collapsing ring 14, and then pushing ring 14, tube portion 22 and flexible member end portion 28 into the orifice until the ring can expand to its relaxed, round shape. The major portions of receiving tube 12 and flexible member 16 remain outside the orifice with member 16 outside the tube. With ring 14 in its relaxed round shape, the receiving tube is secured in the orifice ready to receive excretion. Since tube 12 and member 16 conform to the patient, no irritation is caused.

The device, in the position illustrated in FIG. 2, can be removed from the patient by pulling on the end portion of member 16 extending outside of the body orifice 32. The pulling force exerted on member 16 will cause the ring to rotate approximately 90 degrees, about an axis extending perpendicular to the plane of FIG. 2, relative to the position illustrated in FIG. 2 and to deform and elongate in the direction of removal. Such movement of the ring causes the ring to be oriented such that its smallest dimension extends transversely across orifice 32 minimizing the discomfort experienced by the patient. Thus, the attachment of flexible member 16 to ring 14 greatly facilitates removal of the device from the patient.

Tube 12 has a reduced diameter portion 34 adjacent its closed end 20. This reduced diameter portion facilitates emptying of the tube interior of waste matter without removing device 10 from the patient. Portion 34 can be cut at end 20 to permit the waste material to be emptied into a bedpan. Thereafter, the bag can be closed and resealed by a suitable fastening device commonly used in hospitals and by nurses. Alternatively, device 10 can be replaced in the patient each time it becomes filled.

While certain advantageous embodiment has been chosen to illustrate the invention, it will be understood by those skilled in the art that various changes and modifications can be made therein without departing from the scope of the invention as defined in the appended claims.

What is claimed is:

1. A rectal catheter insertable in a patient's anus for collecting excretions, comprising:
    an excretion receiving tube having an open end and a closed end;
    a solid ring of resilient material fixed to said tube open end; and
    a thin, elongated flexible member means having opposite first and second longitudinal ends, said first end being secured to said ring, said second end being detached from said tube and forming a free end of said flexible member, said flexible member extending exteriorly of said tube from said first end and extending over and into said open end of said tube;
    whereby, the device can be easily removed from the anus of a patient by pulling said flexible member means.

2. A rectal catheter according to claim 1 wherein said first end of said flexible member is attached only along a minor arcuate portion of said ring.

3. A rectal catheter according to claim 1 wherein said first end of said flexible member is attached along an arcuate portion of said ring extending for less than about 90 degrees, but more than about 45 degrees.

4. A rectal catheter according to claim 1 wherein said flexible member comprises a collapsed tube.

5. A rectal catheter according to claim 1 wherein said tube has a reduced transverse diameter portion adjacent said closed end thereof.

6. A rectal catheter insertable in a patient's anus for collecting excretions, comprising:
    an excretion receiving tube having an open end and a closed end;
    a solid ring of resilient material fixed to said tube open end, a first portion of said tube, adjacent said open end thereof, extending about said ring and into said tube and being bonded to said ring providing a smooth exterior surface, and
    a thin, elongated flexible member means having opposite first and second logitudinal ends, said first end being secured to said ring, said second end being detached from said tube and forming a free end of said flexible member, said flexible member extending exteriorly of said tube from said first end;
    whereby, the device can be easily removed from the anus of a patient by pulling said flexible member means.

7. A rectal catheter according to claim 6 wherein said flexible member first end is bonded directly to said ring; and said flexible member overlies said tube first portion.

8. A rectal catheter according to claim 7 wherein said flexible member is bonded only to said ring along a minor arcuate portion thereof.

* * * * *